US00PP37572P3

(12) United States Plant Patent
Beatson

(10) Patent No.: US PP37,572 P3
(45) Date of Patent: Aug. 11, 2026

(54) HOP PLANT NAMED 'CIP014'

(50) Latin Name: ***Humulus lupulus* L.**
Varietal Denomination: CIP014

(71) Applicant: Clayton Hops Limited, Brightwater (NZ)

(72) Inventor: Ronald Alan Beatson, Motueka (NZ)

(73) Assignee: Clayton Hops Limited, Brightwater (NZ)

( * ) Notice: Subject to any disclaimer, the term of this patent is extended or adjusted under 35 U.S.C. 154(b) by 0 days.

(21) Appl. No.: 19/386,575

(22) Filed: Nov. 12, 2025

(65) Prior Publication Data

US 2026/0137015 P1 May 14, 2026

Related U.S. Application Data

(60) Provisional application No. 63/720,235, filed on Nov. 14, 2024.

(51) Int. Cl.
*A01H 6/28* (2018.01)
*A01H 5/00* (2018.01)

(52) U.S. Cl.
USPC ..... Plt./236
CPC ..... *A01H 6/28* (2018.05); *A01H 5/00* (2013.01)

(58) Field of Classification Search
USPC ..... Plt./236
CPC ..... A01H 6/28; A01H 5/00
See application file for complete search history.

*Primary Examiner* — Keith O. Robinson
(74) *Attorney, Agent, or Firm* — Panitch Schwarze Belisario & Nadel LLP; Stephany G. Small; Travis W. Bliss

(57) ABSTRACT

The new hop plant variety 'CIP014' is provided. The new plant variety was produced by crossing '00.L123-22' (the seed parent; not patented) with '05.L202-371' (the pollen parent; not patented) in the course of a planned breeding program. 'CIP014' is characterised by having cones which are late season maturing, with a medium to high alpha acid content, and a high humulene to caryophyllene ratio.

4 Drawing Sheets

Latin name of genus and species of plant claimed: *Humulus lupulus* L.

Variety denomination: 'CIP014'.

STATEMENT REGARDING PRIOR DISCLOSURES BY THE INVENTOR

The first offer for sale of the new plant variety was Dec. 21, 2023, on the Clayton Hops Instagram page. The first offer for sale of the new plant variety was by the inventor or another who obtained the new plant variety directly or indirectly from the inventor. No plants of the new variety have been sold in this country or anywhere in the world, nor has any disclosure of the new plant been made, more than one year prior the effective filing date of this application, and such sale or disclosure within one year was either derived directly or indirectly from the inventor.

BACKGROUND OF THE INVENTION

The new plant variety can be readily distinguished from its ancestors. More specifically, the new plant variety is a triploid whereas the seed parent, '00.L123-22', is a tetraploid and the pollen parent, '05.L202-371', is a diploid. Moreover, the new plant variety can readily be distinguished from other similar non-parental varieties. For example, when compared to 'HORT1524' PACIFIC JADE™ (not patented) and 'Pacific Gem' (not patented), the new plant variety has a later harvest time. In addition, the leaf of the new plant variety has strong blistering of upper side of the blade, wherein as the leaf of 'HORT1524' PACIFIC JADE™ and the leaf of 'Pacific Gem' has weak and absent or very weak, respectively, blistering of the upper side of the blade.

The new variety has been named 'CIP014'. The new variety was previously named 'L14.022-039'. L14.022-039 has also been referred to as the Breeder Code for the new variety.

BRIEF DESCRIPTION OF THE DRAWINGS

The accompanying photographs show as nearly true as it is reasonably possible to make the same, in a color illustration of this character, typical specimens of the new variety.

DETAILED BOTANICAL DESCRIPTION

Figure 1:
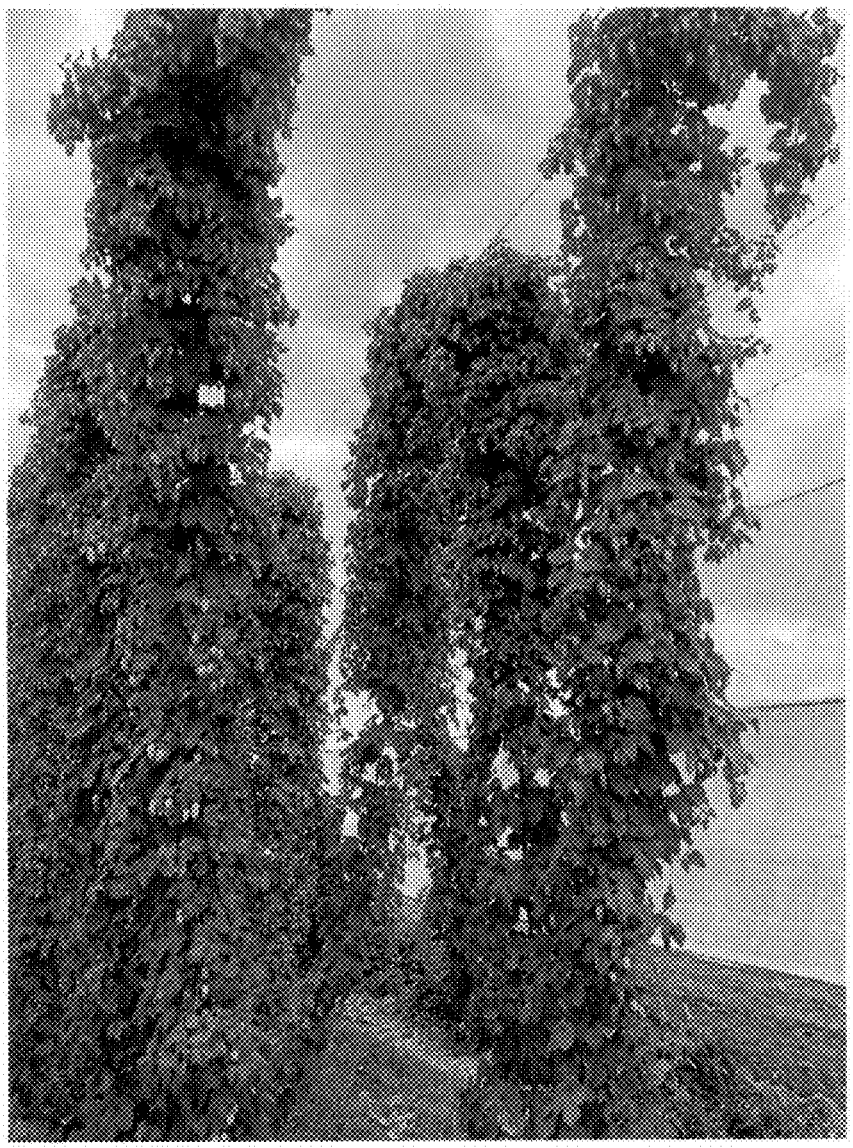
FIG. 1 illustrates three years old specimens of the 'CIP014' plant growing outdoors.
Figure 2:
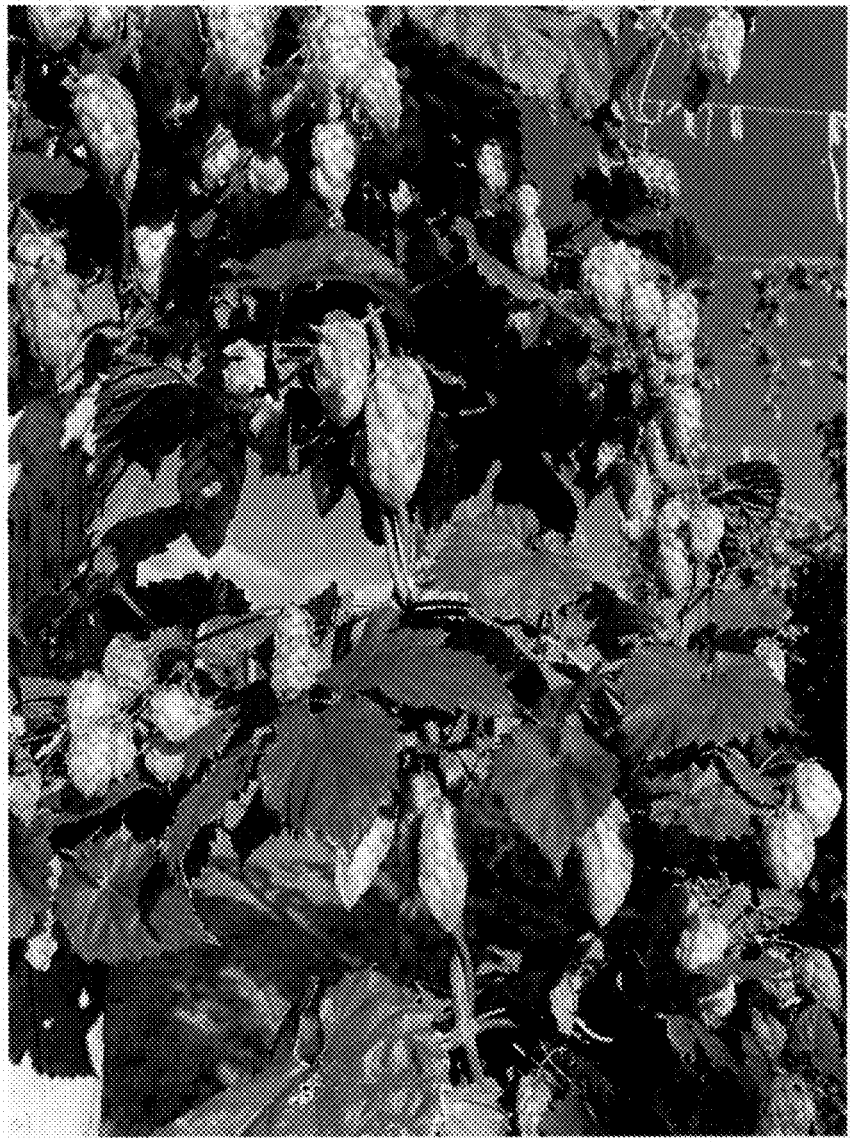
FIG. 2 illustrates specimens of 'CIP014' cones on three years old plant.
Figure 3:
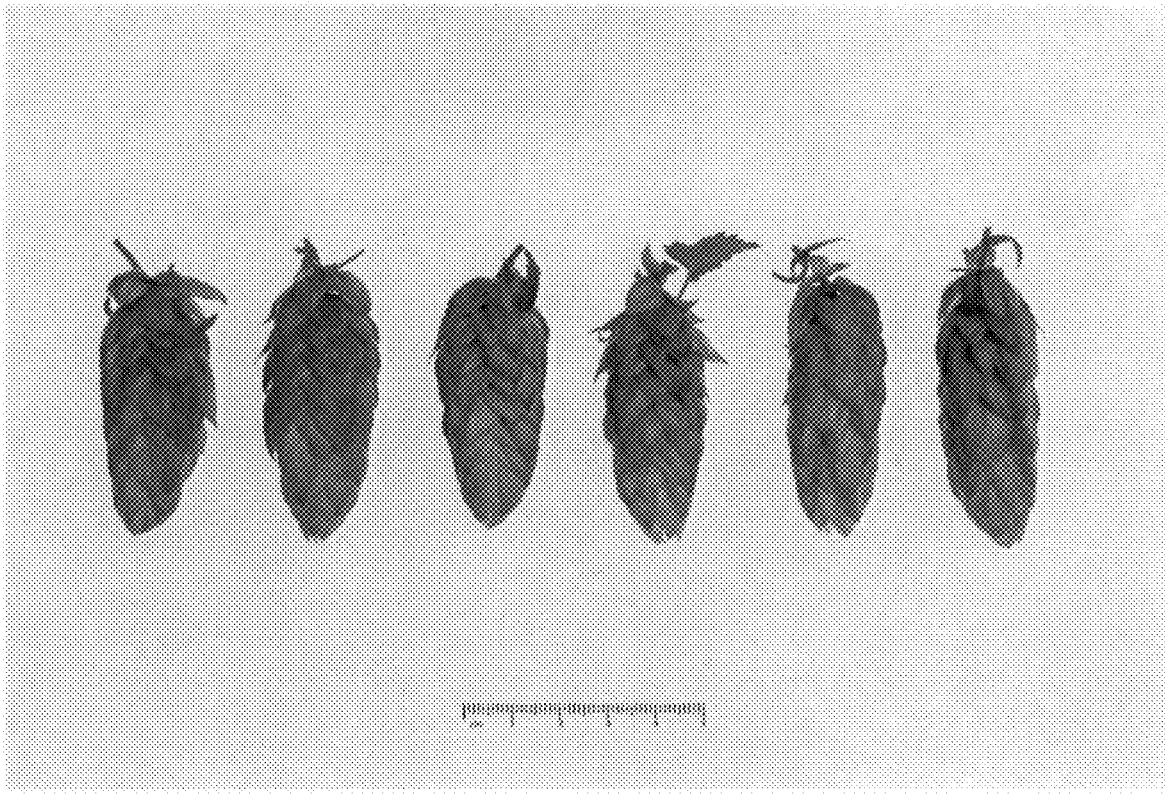
FIG. 3 illustrates specimens of 'CIP014' cones.
Figure 4:
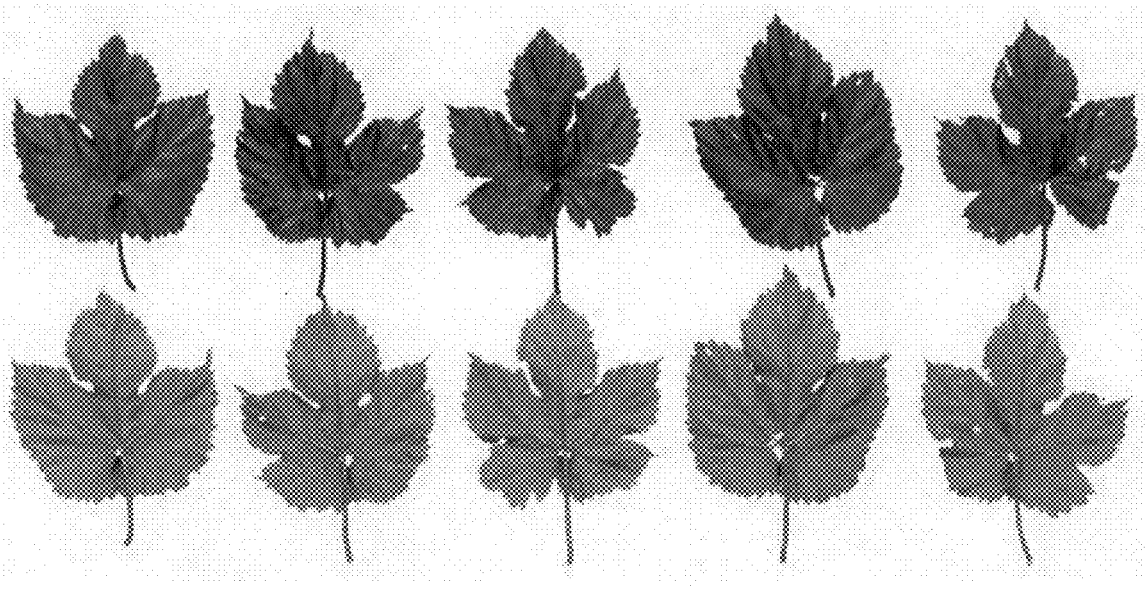
FIG. 4 illustrates specimens of 'CIP014' leaves.

The chart used in the identification of colors is that of The Royal Horticultural Society (The R.H.S. Colour Chart, 2001 edition). The terminology which precedes reference to the chart has been added to indicate the corresponding color in more common terms. The R.H.S. Colour Chart designations used herein represent the closest color observed on the majority of the specified botanical features. The description is based on two to three-years-old specimens of the new plant variety, observed during the 2024-2025 season, while growing in Motueka, New Zealand.

Botanical classification: *Humulus lupulus* L.cultivar 'CIP014'.
Commercial classification: Hop Plant.
Chemical characteristics:

TABLE 1

| Compound | Percentage |
|---|---|
| Alpha acid | 12.2% |
| Beta acid | 5.0% |
| Cohumulone content (as % of Alpha acids) | 28.8% |
| Humulene | 25.3% |
| Farnesene | 0.3% |
| Humulene Caryophyllene ratio | 1:2.979 |

Plant:
*Growth type*.—Normal.
*Shape*.—Cylindrical to club-shaped.
*Volume of head*.—Medium.
Canopy size.—80 cm in diameter and 170 cm in length.
*Plant height*.—Approximately 500 cm.
Average yield.—1.8 tonnes/ha.
*Use*.—Primarily flavouring and bittering ingredient for beer.
Main shoot:
*Anthocyanin coloration*.—Red-Purple Group 59B.
*Background color of upper half*.—Red-Purple Group 60B.
*Intensity of color*.—strong.
*Stripe*.—Present.
*Stripe color*.—Red-Purple Group 60B.
*Node pubescence*.—Weak.
*Vine length*.—Approximately 5.0 m on average.
*Vine diameter*.—Width at base is approximately 9.1 mm on average; width halfway up vine is approximately 8.7 mm on average.
*Internode length*.—Approximately 24.5 cm on average.
*Thorns*.—Present.
*Number of thorns*.—Not observed.
*Anthocyanin coloration of thorns*.—Medium.
*Thorn color*.—Green-Yellow Group 1D.
Lateral shoots:
*Side shoot from middle third of plant*.—Length: approximately 58.6 cm on average. — density of foliage: dense. — number of cones per node: approximately 46.8 on average. — number of nodes per lateral shoot: approximately 7.5 on average.
*Side shoot from upper third of plant*.—Length: approximately 61 cm on average. — number of cones per node: approximately 15.8 on average. — number of nodes per lateral shoot: approximately 16.7 on average. — density of foliage: dense.
*Distribution of lateral shoots*.—Even.
*Attitude of lateral shoots*.—Pendant.
Leaves:
*Size*.—Length is approximately 114.5 mm on average; width is approximately 139.8 mm on average.
*Lobes*.—Present.
*Number of lobes*.—Five.
*Shape of marginal serrations*.—Dentate.
*Basal sinus*.—Medium.
*Depth of basal sinus*.—Medium.
*Lateral sinus*.—Medium.
*Arrangement*.—Opposite.
*Petiole*.—Length: approximately 77.22 mm on average. — width: approximately 2.89 mm on average. — color: Red-Purple Group 61B.
*Blistering of upper side of blade*.—Strong.
*Spines on midrib of under surface*.—Number: medium. — shape: straight.
*Color*.—Upper surface is Green Group 141B.
*Intensity of green color of upper side of blade*.—Medium.
*Glossiness of upper surface*.—Medium.
*Venation*.—Palmate with a color of Yellow-Green Group 145C.
*Stipule*.—Pose: drooping. — size: length is approximately 17.06 mm on average; width is approximately 8.72 mm on average. — shape: triangular. — shape of tip: pointed. — color: Green Group 137C.
Inflorescence:
Flowering:
*Commencement of flowering*.—Medium (December in Motueka, New Zealand).
Cone:
*Length*.—Approximately 40.91 mm on average.
*Width*.—Approximately 19.95 mm on average.
*Shape of longitudinal section*.—Medium ovate.
*Shape of cross section*.—Square.
*Green weight* (*average over* 100).—A range of between 51.0 g to 100.0 g, with an average cone weight of 0.9 g.
*Compactness*.—Open.
*Strig*.—Length: approximately 28.53 mm on average. — width: approximately 2.66 mm on average. — number of nodes: approximately 12 on average. — anthocyanin: absent. — color: Green Group 138B.
*Bract*.—Frequency: few. — size: length is approximately 13.1 mm on average; width is approximately 7.8 mm on average. — ratio width/length: 1.75. — apex length: approximately 1.5 mm on average. — color: Yellow Group 4D. — intensity of green color: medium. — tip shape: mucronate. — tip position: oppressed.
*Bracteole*.—Color: Yellow Group 4D. — length: approximately 13.3 mm on average. — width: approximately 7.4 mm on average.
Development:
*Timing of picking maturing of cones*.—Late (commencing in late March) in Motueka, New Zealand, under normal conditions.
*Pest and disease*.—'CIP014' does not appear particularly resistant or susceptible to pests or diseases known to afflict *Humulus lupulus*.
*Hardiness*.—Zone classification not determined.

The invention claimed is:

1. A new and distinct variety of Hop plant named 'CIP014', substantially as illustrated and described herein.

* * * * *